United States Patent [19]

Mandai et al.

[11] 4,198,534
[45] Apr. 15, 1980

[54] COSMETIC BASE MATERIAL

[75] Inventors: Hiroshi Mandai, Chiba; Anri Tominaga, Tokyo; Yoshikazu Yoshimura, Ichikawa; Hiroshi Isa, Yachiyo, all of Japan

[73] Assignee: The Lion Fat & Oil Co., Ltd., Tokyo, Japan

[21] Appl. No.: 905,126

[22] Filed: May 12, 1978

[30] Foreign Application Priority Data

May 19, 1977 [JP] Japan .................. 52-57086

[51] Int. Cl.$^2$ .......................... C07C 9/14; C07C 3/10
[52] U.S. Cl. ........................ 585/16; 585/18; 585/255; 585/316; 585/510
[58] Field of Search ................ 260/676 R, 683.15 B; 585/16, 18, 255, 316, 510

[56] References Cited

U.S. PATENT DOCUMENTS

| | | | |
|---|---|---|---|
| 3,576,898 | 4/1971 | Blake et al. | 260/676 R |
| 3,778,487 | 12/1973 | Driscoll et al. | 260/676 R |
| 4,017,553 | 4/1977 | Cesca et al. | 260/676 R |
| 4,026,960 | 5/1977 | Nishida et al. | 260/676 R |
| 4,032,588 | 6/1977 | Tomita et al. | 260/676 R |
| 4,032,591 | 6/1977 | Cupples et al. | 260/676 R |
| 4,060,492 | 11/1977 | Yasui et al. | 260/676 R |

*Primary Examiner*—C. Davis
*Attorney, Agent, or Firm*—Blanchard, Flynn, Thiel, Boutell & Tanis

[57] ABSTRACT

A cosmetic base material which consists of a synthetic saturated aliphatic hydrocarbon having 24 to 36 carbon atoms, wherein the proton ratio of methyl group to methylene group, that is, $CH_3/CH_2$, within the hydrocarbon chain is in the range of from 0.25 to 0.6 and the pour point is in the range of from $-55°$ C. to $10°$ C.

1 Claim, No Drawings

COSMETIC BASE MATERIAL

BACKGROUND OF THE INVENTION

The present invention relates to a cosmetic base material, and particularly it relates to a cosmetic base material which imparts a comfortable feel to cosmetics when mixed therewith and is chemically stable.

Cosmetics generally comprise an ingredient for imparting an appropriate oiliness thereto as base material. As cosmetic base materials for this purpose, liquid paraffin, squalene, fatty acid ester, etc. have hitherto been prevalently employed. Among these substances, fatty acid esters represented by isopropyl myristate (IPM), isopropyl palmitate (IPP), 2-octyl dodecanyl myristate (MOD), etc. are popular as base material capable of imparting a good feel to cosmetics. However, because the ester bond is vulnerable to hydrolysis, cosmetics comprising fatty acid esters have drawbacks such that the emulsion state thereof is apt to be destroyed or they give out an offensive smell. On the other hand, liquid paraffin, squalene, etc. are admittedly chemically stable, but even squalene which is reputed to be agreeable to the touch is inferior to fatty acid esters in respect of the feel.

In the case of saturated aliphatic hydrocarbons derived from petroleum or animals and plants, the structure and properties thereof are limited so that they are insufficient in respect of the efficiency required for cosmetic base materials. Therefore, it will be very convenient if synthetic saturated aliphatic hydrocarbons, which are easily available, have an aptitude to serve as a cosmetic base material. In fact, paraffins having 22 or more carbon atoms are known to be non-irritative to the skin.

SUMMARY OF THE INVENTION

The present inventors have made a series of studies of synthetic saturated aliphatic hydrocarbons which are not irritative to the skin, and as a result, they have come to a finding that, among saturated aliphatic hydrocarbons obtained by hydrogenating liquid oligomers of olefins, hydrocarbons having 24 to 36 carbon atoms wherein the proton ratio of methyl group to methylene group, that is, $CH_3/CH_2$, within the hydrocarbon chain thereof is in the range of from 0.25 to 0.6 and the pour point is in the range of from $-55°$ C. to $10°$ C. (according to Japanese Industrial Standards K2269 (ASTM D-97) concerning pour point; the same applies to the following) are best suited for use as a cosmetic base material. Since these synthetic saturated aliphatic hydrocarbons are chemically stable, admixing of them with other cosmetic ingredients will produce cosmetics which make the users feel refreshed and are free from deterioration in quality despite prolonged storage.

In the case of a hydrocarbon in which the proton ratio of methyl group to methylene group is less than 0.25, it is apt to crystallize so that it is incapable of imparting a good feel to cosmetics, while in the case of a hydrocarbon in which said proton ratio exceeds 0.6, branching therein is excessive so that the storage stability of the product cosmetic is impaired and the feel thereof deteriorates. It is for the same reason that limits to the pour point are set as described above: that is, in the case of a hydrocarbon having a pour point exceeding $10°$ C., it presents wax-like conditions so that it fails to impart a comfortable feel to cosmetics, while in the case of a hydrocarbon having a pour point of less than $-55°$ C., it deteriorates the feel of cosmetics.

DETAILED DESCRIPTION OF THE INVENTION

A cosmetic base material according to the present invention can be prepared through the process comprising dimerizing aliphatic mono-olefins having 12 to 18 carbon atoms and hydrogenating the resulting dimers. In the case of a saturated hydrocarbon obtained by dimerizing a mono-olefin having 19 or more carbon atoms followed by hydrogenation, it presents wax-like conditions with high viscosity as well as high pour point so that it lacks aptitude for use as a cosmetic base material, while in the case of a saturated hydrocarbon obtained from a mono-olefin having 11 or less carbon atoms, it is undesirable for use as cosmetic base material because it is irritative to the skin. Consequently, to give examples of starting material olefins suitable for preparing the cosmetic base material of the present invention by dimerizing mono-olefins and hydrogenating thereafter, there are 1-dodecene, 1-tridecene, 1-pentadecene, 1-hexadecene, 1-heptadecene, 1-octadecene (the foregoing are $\alpha$-olefins), 3-methyl undecene-1, 4-ethylene decene-1, 4-methyl tridecene-1, 3-ethyl tridecene-1, 5-propyl heptadecene-1, 6-butyl tridecene-1, 4-methyl hexadecene-1, 2,6-dimethyl tridecene-1 (the foregoing are branched $\alpha$-olefins), 2-methyl undecene-1, 2-propyl decene-1, 2-butyl decene-1, 2-hexyl octene-1, 2-octyl nonene-1, 2-propyl pentadecene-1 (the foregoing are vinylidene olefins), 2,6-dimethyl undecene-1, 2,3-methyl ethyl decene-1, 2,5-ethyl propyl decene-1 (the foregoing are branched vinylidene olefins), dodecene-2, dodecene-3, dodecene-5, tridecene-3, tridecene-6, pentadecene-3, hexadecene-2, heptadecene-4, octadecene-8 (the foregoing are internal olefins), 2-methyl hexadecene-4, 3-propyl pentadecene-5 (the foregoing are branched internal olefins), etc. Further, these olefins can be oligomerized by admixing two or more of them. The dimer for use in the present invention is not always required to be a dimer of identical olefins, that is, it can be a dimer obtained by reacting different olefins.

The cosmetic base material in the present invention can be prepared by subjecting olefins either to cationic polymerization employing Lewis acid catalyst or Lewis acid/Lewis base complex catalyst or to group polymerization, coordinated anionic polymerization, etc. through optional known processes, taking out the resulting dimer, and then hydrogenating said dimer. Especially, it can be profitably prepared through the process comprising oligomerizing aliphatic mono-olefins having 12 to 18 carbon atoms, separating unreacted olefin from by-product olefin polymers other than the dimer, such as the trimer, tetramer and so on, by distillation, and hydrogenating the thus obtained dimer by a conventional method. Synthetic saturated aliphatic hydrocarbons having 24 to 36 carbon atoms prepared by this cationic polymerization method meet the aforementioned requirements in respect of both the proton ratio of methyl group to methylene group and the pour point so that they are particularly suitable for use as a cosmetic base material. As the hydrogenation catalyst for use in hydrogenating a dimer of aliphatic mono-olefins, there are available known catalysts such as nickel on diatomaceous earth, Raney nickel, active carbon-platinum, active carbon-palladium, etc.

The cosmetic base material according to the present invention can be used in the same way as in the case of the conventional cosmetic base materials. Shown in Table-1 in the following are cosmetic compositions comprising a cosmetic base material according to the present invention as applied to a cleansing cream (A), cold cream (B), anti-tanning cream (C) and foundation cream (D) which constitute typical cosmetics, but the use of the present cosmetic base material is of course not limited to these.

Table 1

| Cosmetic ingredient | Cosmetic Compositions (wt.%) | | | |
|---|---|---|---|---|
| | A | B | C | D |
| base material | 41.0 | 38.0 | 22.0 | 27.0 |
| beeswax | 3.0 | 12.0 | 15.0 | — |
| solid paraffin | 10.0 | 7.0 | — | 5.0 |
| vaseline | 15.0 | 10.0 | 31.0 | — |
| lanolin | — | 3.0 | — | 10.0 |
| sorbitan sesquioleate | 4.2 | 3.8 | 4.0 | 5.0 |
| polyoxyethylene sorbitan monooleate | 0.8 | 0.2 | — | — |
| ethyl para-aminobenzoate | — | — | 2.0 | — |
| powder coloring agent | — | — | — | 35.0 |
| perfume | 1.0 | 0.5 | 1.0 | 0.5 |
| purified water | 25.8 | 25.5 | 25.0 | 17.5 |
| antioxidant, preservatives | a proper dose | a proper dose | a proper dose | a proper dose |

As elucidated in the foregoing, the cosmetic base material under the present invention consists of synthetic saturated aliphatic hydrocarbon having a specific number of carbon atoms, and the proton ratio of methyl group to methylene group and the pour point thereof are in a specific range respectively, so it is not only chemically stable but also possessed of oily feel. Consequently, cosmetics comprising the present base material make the users feel refreshed and ensure storage stability over a long period of time.

EXAMPLE 200 g each of various aliphatic mono-olefins having 12 or more carbon atoms such as shown in the following Table-2 were put in a glass receptacle after replacing the air therein with dry nitrogen, and 1 hour's reaction was effected at a temperature of 120° C. in the presence of 1 g of anhydrous aluminum chloride. After completing the reaction, the catalyst was decomposed by blowing ammonia gas into the reactor, the thus decomposed catalyst was filtered, and then the reaction product was distilled, whereby a dimer was obtained. Subsequently, by hydrogenating this dimer under hydrogen pressure of 50 Kg/cm$^2$ in the presence of 2 g of nickel-kieselguhr catalyst, a cosmetic base material according to the present invention was obtained.

The thus obtained base material and the conventional cosmetic base materials were subjected to measurement of their proton ratio of methyl group to methylene group by the nuclear magnetic resonance method and of their pour point by applying JIS K2216 (ASTM D-97), and further subjected to comparison of their feel as well as stability when left alone by the following method. The result was as shown in Table-2 below.

(a) Test of the feel:

A small quantity of each base material was applied to the upper arm of every one of 25 men and 40 women, and the feel of every base material was awarded points on the basis of 10 for a base material which felt best (namely, isopropyl myristate) and 1 for a base material which felt most sticky and uncomfortable (namely, vaseline). Then, by averaging the points thus awarded, the examination points of the respective base materials were calculated.

(b) Test of the stability when left alone:

Each base material was left alone in a thermostat set at a temperature of 45° C. for 100 days, and the odor and acid value before and after thus leaving alone were examined.

Table 2

| | Base material or starting material therefore | Properties of Base Materials | | | | | | |
|---|---|---|---|---|---|---|---|---|
| | | $CH_3/CH_2$ | Pour point °C. | Rating of feel | Before leaving alone | | After leaving alone | |
| | | | | | odor | acid value | odor | acid value |
| Example under present invention | 1-dodecene | 0.314 | −50.0 | 9.6 | odorless | <0.01 | odorless | <0.01 |
| | 1-pentadecene | 0.276 | −20.0 | 9.5 | odorless | <0.01 | odorless | <0.01 |
| | 1-hexadecene | 0.285 | −12.5 | 9.9 | odorless | <0.01 | odorless | <0.01 |
| | 1-octadecene | 0.265 | 0.0 | 9.6 | odorless | <0.01 | odorless | <0.01 |
| | 2-methyl undecene | 0.281 | −50.0 | 9.7 | odorless | <0.01 | odorless | <0.01 |
| | 2-butyl decene | 0.292 | −50.0 | 9.5 | odorless | <0.01 | odorless | <0.01 |
| | dodecene-2 | 0.303 | −47.5 | 9.4 | odorless | <0.01 | odorless | <0.01 |
| | tridecene-3 | 0.279 | −45.0 | 9.3 | odorless | <0.01 | odorless | <0.01 |
| | 2-methyl dodecene-2 | 0.552 | −42.5 | 9.7 | odorless | <0.01 | odorless | <0.01 |
| | 1-tetradecene | 0.36 | −27.5 | 9.6 | odorless | <0.01 | odorless | <0.01 |
| Comparative Example | 2,5,8-trimethyl nonene-1 | 1.19 | <−60 | 5.0 | odorless | <0.01 | trace of odor | 0.01 |
| | polybutene | 1.32 | −35.0 | 5.6 | odorless | 0.01 | odorless | 0.01 |
| | isopropyl myristate | — | | 10.0 | odorless | 0.01 | strong smell | 3.2 |
| | isopropyl palmitate | — | | 9.7 | odorless | 0.01 | strong smell | 2.9 |
| | 2-octyl dodecanyl myristate | — | | 7.4 | odorless | 0.01 | odorless | 1.8 |
| | liquid paraffin | 0.49 | −7.5 | 4.1 | odorless | 0.01 | odorless | 0.01 |
| | squalene | 0.75 | −60.0 | 6.9 | odorless | 0.01 | trace of | 0.03 |

Table 2-continued

| Base material or starting material therefore | Properties of Base Materials | | | | | | |
|---|---|---|---|---|---|---|---|
| | CH$_3$/CH$_2$ | Pour point °C. | Rating of feel | Before leaving alone | | After leaving alone | |
| | | | | odor | acid value | odor | acid value |
| | | | | | | odor | |

As is evident from the foregong table, a cosmetic base material according to the present invention has a feel comparing with isopropyl myristate which has been reputed to have the best feel, and as for the stability thereof when left alone, it surpasses liquid paraffin.

What is claimed is:

1. A cosmetic base material consisting of synthetic saturated aliphatic hydrocarbon having from 24 to 36 carbon atoms in the molecule, a methyl/methylene proton ratio of from 0.25/1 to 0.6/1 and a pour point of from −55° C. to 10° C., said synthetic saturated aliphatic hydrocarbon having been prepared by cationic polymerization of an aliphatic monoolefin having from 12 to 18 carbon atoms in the monoolefin molecule or mixture of said monoolefins, separating the dimer formed by said cationic polymerization from unreacted olefin and oligomers of higher degree of polymerization than the dimer, and then hydrogenating said dimer to obtain said cosmetic base material.

* * * * *